US00PP29309P2

(12) United States Plant Patent
Klemm et al.

(10) Patent No.: US PP29,309 P2
(45) Date of Patent: May 22, 2018

(54) ***PETUNIA* PLANT NAMED 'KLEPH16332'**

(50) Latin Name: *Petunia hybrida*
Varietal Denomination: KLEPH16332

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days. days.

(21) Appl. No.: 15/731,047

(22) Filed: Apr. 10, 2017

(51) Int. Cl.
*A01H 5/02* (2018.01)

(52) U.S. Cl.
USPC ..... Plt./356.13

(58) Field of Classification Search
USPC ..... Plt./356.13
See application file for complete search history.

*Primary Examiner* — Annette H Para
(74) *Attorney, Agent, or Firm* — Barbara Campbell; Bethany R. Roahrig; Cochran Freund & Young LLC

(57) ABSTRACT

A new *Petunia* plant particularly distinguished white flowers with purple-violet stripes and greyed-green veins and a mounding to semi-trailing habit, is disclosed.

1 Drawing Sheet

Genus and species: *Petunia hybrida.*
Variety denomination: 'KLEPH16332'.

BACKGROUND OF THE NEW PLANT

The present invention comprises a new and distinct variety of *Petunia*, botanically known as *Petunia hybrida*, and hereinafter referred to by the variety name 'KLEPH16332'. 'KLEPH16332' originated from a cross-pollination conducted in July 2013 in Latina, Italy between the female *Petunia* variety 'Peppy Blue' (patent status unknown) and the proprietary male *Petunia* variety 'PH-2013-4376' (unpatented).

The seeds from the cross were sown and plants were grown in a greenhouse for evaluation, where an individual plant designated 'KLEPH16332' was selected from the group of plants in April 2014 in Latina, Italy. In May 2014, 'KLEPH16332' was first vegetatively propagated by terminal tip cuttings. 'KLEPH16332' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. White flowers with purple-violet stripes and greyed-green veins; and
2. A mounding to semi-trailing habit.

DESCRIPTION OF THE PHOTOGRAPH

This new *Petunia* plant is illustrated by the accompanying photograph of a plant grown in a plastic greenhouse in Stuttgart, Germany. The photograph was taken in April 2015 and shows the foliage and flowers of an 8-week-old plant grown in a pot. The colors shown are as true as can be reasonably obtained by conventional photographic procedures.

DESCRIPTION OF THE NEW VARIETY

The following detailed descriptions set forth the distinctive characteristics of 'KLEPH16332'. The data which define these characteristics were collected from asexual reproductions carried out in Latina, Italy. Data was collected on plants grown 13-weeks from cultivation from potting in a plastic greenhouse in Latina, Italy in March 2017. Color references are to The R.H.S. Colour Chart of The Royal Horticultural Society of London (R.H.S.), 5$^{th}$ edition (2007).

Classification:
- *Family.*—Solanaceae.
- *Botanical.*—*Petunia hybrida.*
- *Common.*—*Petunia.*
- *Designation.*—'KLEPH16332'.

Parentage:
- *Female parent.*—The female *Petunia* variety 'Peppy Blue' (patent status unknown).
- *Male parent.*—The proprietary male *Petunia* variety 'PH-2013-4376' (unpatented).

Plant:
- *Vigor.*—Medium vigor.
- *Habit.*—Mounding to semi-trailing.
- *Height* (*from top of soil*).—6.0 cm.
- *Width* (*horizontal plant diameter*).—22.0 cm.
- *Propagation.*—Terminal tip cuttings and tissue culture.
- *Time to produce a finished flowering plant.*—About 13 weeks in the winter under short day conditions, and 5 weeks in the spring.
- *Time to initiate and develop roots.*—2 to 3 weeks.
- *Root description.*—Moderate density, moderate branching, white roots.

Stems:

*Average number* (*basal*).—12.

*Length of basal branches* (*from the base of the stem to the tip*).—14.0 cm.

*Internode length*.—1.0 cm to 2.5 cm.

*Diameter of branches* (*from midpoint*).—0.5 cm.

*Stem color*.—RHS 144B.

*Anthocyanin*.—Absent.

*Texture*.—Tomentose.

Leaves:

*Arrangement*.—Alternate.

*Length*.—5.5 cm.

*Width*.—4.0 cm.

*Shape*.—Circular and obovate.

*Apex*.—Obtuse, slightly mucronate.

*Base*.—Attenuate.

*Margin*.—Entire.

*Immature leaf color*.—Upper surface: RHS N137B. Lower surface: RHS 138B.

*Mature leaf color*.—Upper surface: RHS 137B. Lower surface: RHS 138B.

*Texture* (*both upper and lower surfaces*).—Slightly tomentose.

*Venation pattern*.—Arcuate.

*Venation color*.—Upper surface: RHS 137C. Lower surface: RHS 143C.

*Petioles*.—Length: 0.2 cm. Diameter: 0.3 cm. Color: Varies between RHS 144C and RHS 144D. Texture: Tomentose.

Flower buds:

*Shape*.—Irregular oblong.

*Length*.—About 3.5 cm.

*Diameter*.—0.6 cm.

*Color at tight bud*.—Between RHS 76A to RHS N81A and RHS N77A.

*Texture*.—Slightly tomentose.

Inflorescence:

*Blooming habit* (*flowering season*).—Continuous flowering during spring and summer time.

*Inflorescence type*.—Sympodial, with monochasial growth.

*Number of flowers per node*.—1.

*Lastingness of individual blooms on the plant*.—7 to 10 days.

*Fragrance*.—Not detected.

*Flowers*.—Arrangement: Composed of 5 petals fused at the base. Diameter (flower face): 5.5 cm. Depth (total length of flower): 5.2 cm. Throat/Funnel: Length: About 3.0 cm. Diameter (at opening): About 1.0 cm. Texture: Inner surface: Smooth. Outer surface: Slightly pubescent. Color: Inner surface: The inner surface is covered with numerous dense veins, so the inner throat color is the color of the veins, RHS N177A. Outer surface: RHS N77D and RHS N77A veins. Petals: Color of petals, mature flower (fully opened): Upper surface: Varies between RHS N81A and RHS N80A for the stripes, RHS N155D for the flower color, and RHS 195A for the veins. Lower surface: RHS N82A for the stripes, RHS N155D for the flower color, and RHS 197B for the veins. Apex: Slightly emarginate. Base: Fused. Shape: Funnelform. Margin: Entire. Strength of waviness: Weak. Degree of lobation: Weak. Calyx arrangement: Actinomorphic, composed of 5 sepals. Sepals: Color: Upper surface: RHS N137B. Lower surface: RHS 137C. Length: About 2.0 cm. Width: 0.7 cm. Shape: Spatulate. Apex: Slightly mucronate. Base: Attenuate. Margin: Entire. Texture (both upper and lower surfaces): Slightly pubescent.

*Pedicels*.—Color: Varies between RHS 144B and RHS 144C. Length: 2.3 cm. Diameter: 0.2 cm. Texture: Tomentose.

Reproductive organs:

*Stamens*.—Quantity: 5. Shape: Needle with elliptic head. Filament: Length: 0.9 cm to 1.3 cm. Diameter: 0.05 cm. Color: Varies between RHS 85C and RHS 85D. Anther: Shape: Ovate. Color: RHS 91B. Length: 0.3 cm. Diameter: 0.2 cm. Pollen: Color: RHS 97A. Amount: Moderate.

*Pistils*.—Quantity per flower: 1. Length: 2.0 cm. Stigma color: RHS 144A. Style color: RHS 149C at the base and RHS N79A at the top.

Fruit and seed set: No fruit and seed set observed.

Disease and pest/insect resistance: No disease and pest/insect resistance observed.

COMPARISON WITH PARENTAL LINES AND KNOWN VARIETY

'KLEPH16332' is a distinct variety of *Petunia* and is distinguished from its parents as described in Table 1.

TABLE 1

Comparison with Parental Lines

| Characteristic | 'KLEPH16332' | Female Parent 'Peppy Blue' | Male Parent 'PH-2013-4376' |
|---|---|---|---|
| Earliness | About 10 days earlier than 'Peppy Blue' | About 10 days later than 'KLEPH16332' | |
| Flower color | White flowers with purple-violet stripes and greyed-green veins | | White |

'KLEPH16332' is a distinct variety of *Petunia* and differences between 'KLEPH16332' and the commercial variety, also the female parent, 'Peppy Blue' are described in Table 2.

TABLE 2

Comparison with Similar Variety

| Characteristic | 'KLEPH16332' | 'Peppy Blue' |
|---|---|---|
| Earliness | About 10 days earlier than 'Peppy Neon' | About 10 days later than 'KLEPH16332' |

We claim:

1. A new and distinct variety of *Petunia* plant designated 'KLEPH16332' as illustrated and described herein.

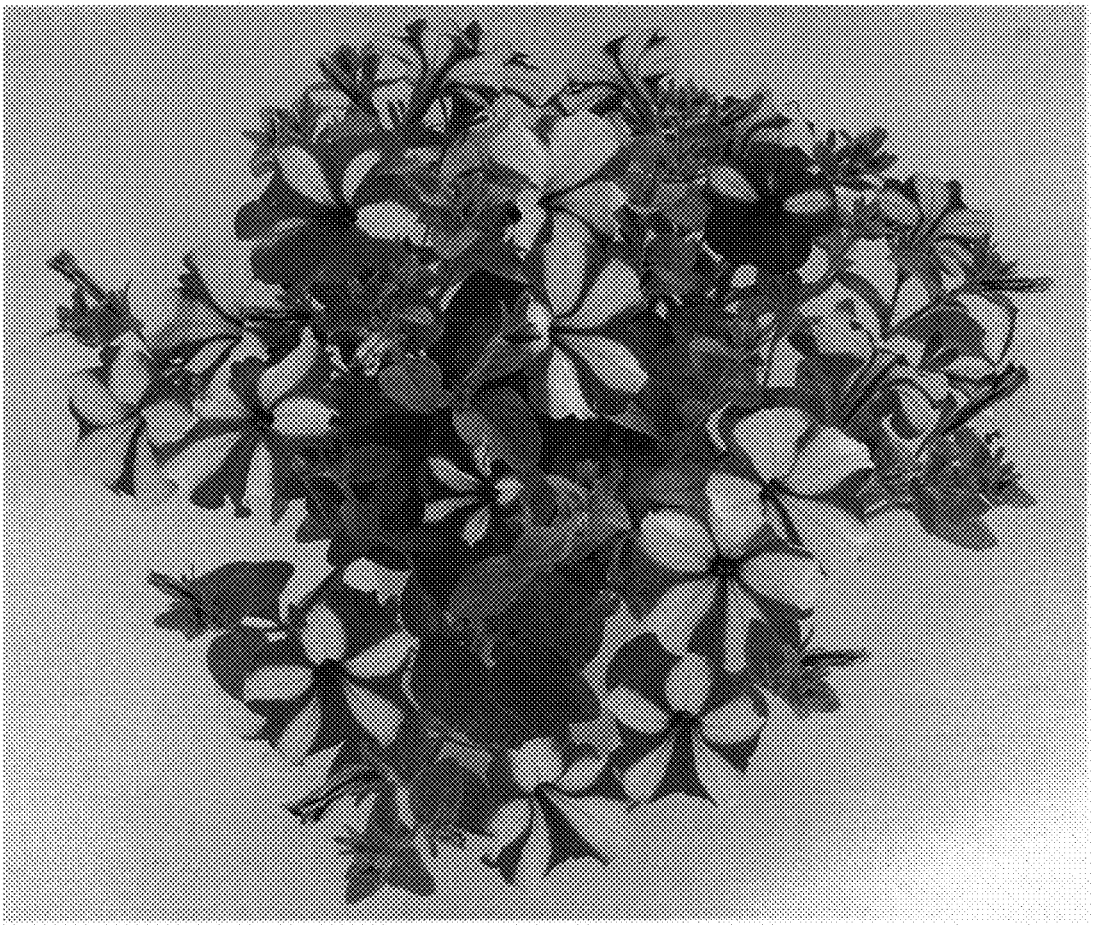

* * * * *